United States Patent [19]

Reinicke

[11] Patent Number: 4,626,244

[45] Date of Patent: Dec. 2, 1986

[54] IMPLANTABLE MEDICATION INFUSION DEVICE

[75] Inventor: Robert H. Reinicke, Mission Viejo, Calif.

[73] Assignee: Consolidated Controls Corporation, El Segundo, Calif.

[21] Appl. No.: 697,514

[22] Filed: Feb. 1, 1985

[51] Int. Cl.⁴ ............................................... A61M 5/00
[52] U.S. Cl. .................................... 604/141; 604/151; 604/891; 128/DIG. 12
[58] Field of Search ..................... 604/51–53, 604/131, 132, 141, 151, 890–892, 896; 128/DIG. 12

[56] References Cited

U.S. PATENT DOCUMENTS

| | | | |
|---|---|---|---|
| 3,731,681 | 5/1973 | Blackshear et al. | 604/141 |
| 4,140,122 | 2/1979 | Kuhl et al. | 604/891 |
| 4,221,219 | 9/1980 | Tucker | 604/141 |
| 4,360,019 | 11/1982 | Portner et al. | 604/891 X |
| 4,496,393 | 1/1985 | Prosl et al. | 604/141 |
| 4,511,355 | 4/1985 | Franetzki et al. | 604/891 X |

Primary Examiner—Stephen C. Pellegrino
Attorney, Agent, or Firm—Mason, Kolehmainen, Rathburn & Wyss

[57] ABSTRACT

An integral fluid filter and capillary restrictor unit, or alternatively an integral fluid filter and multiple orifice restrictor unit, is resiliently positioned in a manifold body which is edge mounted to a flat cylindrical assembly which contains the medication reservoir and pressure stabilizing chamber to provide a completely self contained implantable unit which is thin, small and light weight and yet needs to be refilled only as often as the much larger stainless steel capillary tube devices with bellows type reservoirs now on the market.

32 Claims, 12 Drawing Figures

IMPLANTABLE MEDICATION INFUSION DEVICE

BACKGROUND OF THE INVENTION

The present invention relates to implantable medication infusion devices, and, more particularly to such devices which are arranged to provide a continuous unprogrammed flow of medication into the body.

Medication infusion devices of the continuous flow type shown in Blackshear et al U.S. Pat. No. 3,731,681 and in the article by B. M. Wright entitled "A Portable Slow Infusion Capsule" in the Journal of Physiology March 1965, Vol. 177 No. 1 (Cambridge University Press) and devices similar to the Blackshear patent are presently available on the market. In such devices a relatively constant pressure is exerted on a flexible diaphragm or bellows which contains a reservoir of medication. The pressure exerted on the bellows is above body pressure so that medication is forced out of a long capillary tube, which is used as a flow limiting resistance device, and delivered to the infusion site within the body. This capillary tube is usually made of stainless steel and a length of 50 feet may be required to provide sufficient resistance to flow for desired delivery rates of medication even when the tube is fabricated to the minimum practical inside diameter of 0.004 inches. This stainless steel capillary tube is wrapped around the outside of the implantable device, or in a recess in the outside of the housing of such device as shown in Blackshear U.S. Pat. No. 3,731,681, and the end of the capillary tube is connected to a flexible catheter which is positioned at the infusion site in the body.

When such a long stainless steel capillary tube is used the medication remains in contact with the stainless steel for many hours, or even days, at relatively low infusion rates and this long residence or dwell time within the capillary tube causes problems of compatibility with the medication, particularly when a medication such as insulin is used. When a stainless steel capillary tube is used the medication is also more likely to precipitate out and clog the capillary tube. While titanium is more compatible to the medication and is less likely to clog, it is impossible to fabricate a titanium capillary tube of such small diameter. When it is desired to provide different flow rates with such a stainless steel capillary tube, each device must be tested separately after it is manufactured and the length of the capillary tube is trimmed down and then retested to get a particular infusion rate.

It is often necessary to mix the medication with a high viscosity diluent for use in existing continuous infusion devices in order to limit the capillary tube to a practical length, such as 50 feet. Using a high viscosity diluent makes the medication less potent while increasing the viscosity of the medication solution, and since capillary tube length is directly proportional to medication solution potency and inversely proportional to its viscosity, both of these effects reduce the length of capillary tube. For example, it is not feasible to deliver standard, undiluted 100 unit insulin to diabetic patients with existing devices. By diluting 100 unit insulin with 80% glycerol it is possible to use these devices but they must have large (typically 30 to 50 milliliters) reservoirs to contain the diluted medication and such a large reservoir requires the use of a flexible multiple convolution bellows rather than a single diaphragm, thus making the devices large and heavy and not suitable for implantation in children and less than average size adults. Such bellows type devices suffer from the additional disadvantage that they have many crevices ano a much higher residual and unusable medication volume than the diaphragm type of reservoir.

The infusion rate of existing continuous infusion devices also varies considerably due to changes to patient body pressure and changes in patient body temperature. Body pressure change, which varies the pressure at the outlet of the catheter and capillary tube restrictor, is due to variations in altitude which changes the ambient atmospheric and body pressure of the patient. Also, normal small changes (as well as abnormal changes due to sickness) in patient body temperature change the vapor pressure of the medication reservoir pressurant, thus changing the pressure at the inlet of the capillary tube restrictor. Therefore, both altitude and temperature changes act to vary the pressure drop across the capillary tube restrictor and the infusion rate through the capillary tube, which is directly proportional to this pressure drop. For example, if the patient travels from sea level to 10,000 feet above sea level, the drug infusion rate of existing devices increases by a factor of 2.5. If the patient temperature should also happen to increase from 97° F. to 101° F., the combined effect of the altitude and temperature changes would increase the infusion rate by a factor of 3.5. This large infusion rate variation can severely limit the clinical effectiveness and benefits for many continuous drug infusion treatments.

In Barth application Ser. No. 616,658 filed June 4, 1984 an integral fluid filter and capillary arrangement is disclosed in which the capillary is formed by a groove etched in the surface of silicon substrate by conventional semiconductor processing techniques and a glass plate is bonded to said surface of the substrate to form a long capillary groove of very small cross sectional area. A plurality of parallel grooves of smaller cross sectional area are also etched in the substrate surface to provide a comb filter at each end of the capillary groove.

SUMMARY OF THE INVENTION

The arrangement of the present invention avoids all of the above discussed difficulties experienced with a stainless steel capillary tube by employing an integral fluid filter and capillary groove restrictor arrangement generally similar to that described in said Barth application, or, in the alternative, an integral filter and multiple orifice restrictor arrangement. The integral fluid filter and restrictor unit is resiliently positioned in a manifold body which is edge mounted to a flat cylindrical assembly which contains the medication reservoir and pressure stabilizing chamber to provide a completely self contained implantable unit which is thin, small and light weight and yet needs to be refilled only as often as the much larger stainless steel capillary tube devices with bellows type reservoirs now on the market. The silicon and glass surfaces of the integral filter and restrictor unit are highly compatible with medication such as insulin. Also, due to the extremely small, precise cross sectional area of the restrictor groove in the silicon substrate a much greater restriction per unit length is provided so that the overall restriction is much greater while greatly reducing the overall length of the restrictor groove with a corresponding reduction of the dwell time of the medication within the restrictor groove. As a result, full strength medication, such as insulin, may be utilized in the reservoir of the implantable device so that the reservoir is much smaller, thus making the device much smaller and lighter than devices now available which have large reservoirs to contain diluted (as much as 80%) medication. Furthermore, the use of maximum strength medication, such as insulin, facilitates the provision of a lower medication delivery rate so that a smaller volume reservoir in the device of the present invention lasts as long as the much larger devices now being used before refill is needed. For example, with a restrictor groove of only 6.4 inches total length sufficient flow restriction is provided to give a continuous flow rate of 10 microliters per hour of 100 unit insulin and the insulin is within the flow restrictor groove for only about 80 seconds. The 10 microliters per hour of 100 unit insulin used in this example delivers 1 unit per hour of insulin, which is the nominal basal infusion rate required for Type I diabetics.

Since the silicon and glass integral filter and restrictor groove unit can be manufactured with minimum feature sizes of only a few microns (micrometers), it is very easy to fabricate miniature restrictor units that are much more restrictive than needed for the delivery of standard, full strength medications that are now commercially available. Therefore, with the arrangement of the present invention, pharmaceutical drug suppliers will have a market for more potent medications so that the implantable devices can be made even smaller and lighter, and then could be used by children and even infants.

With such an integral filter and restrictor unit it is also possible to use a different two phase pressurant having a greater vapor pressure (which requires a more restrictive integral filter and restrictor unit) in the stabilizing chamber of the drug reservoir to reduce the undesirable variation of infusion rate due to altitude and temperature changes. For example, the aforementioned 2.5 factor increase of infusion rate when the patient travels from sea level to 10,000 feet altitude is reduced to a factor of 1.5 by using Freon 11, also called Freon MF, (vapor pressure equal to 23 psia at 98.6° F.) produced by E. I. DuPont Company, in place of the FC-87 or FC-88 Perfluorocarbon (vapor pressure equal to 17.5 psia at 98.6° F.), produced by the 3M Company, now being used. Although there is a slight weight increase because of the stiffer structure needed to contain the higher pressure, this device is still much lighter than existing devices.

In accordance with a further aspect of the invention, the infusion rate variation can also be reduced by replacing the capillary type groove with a series of miniature orifices, since flow rate through an orifice is proportional to the square root of its pressure drop, not directly proportional as in a capillary. But because the infusion rate is extremely small, its velocity pressure is quite low, the orifices must be very small and many orifices are needed in series to create sufficient pressure drop. For example, using anisotropic etched orifices each having a maximum feature dimension of only 8 microns, 2530 series orifices are needed to limit the infusion rate to 10 microliters per hour using FC-87 or FC-88 Perfluorocarbon pressurant at normal body temperature, 98.6° F. It is not possible to use conventional metal machining or metal chemical milling processes to fabricate this very small size and large number of orifices in a metal such as titanium. However, miniature precision orifices can be easily fabricated in silicon using standard lithography and masking processes that are used to manufacture solid state electronic chips and micromachining techniques such as described in an article entitled "Silicon Micromechanical Devices" by James B. Angell, Stephen C. Terry and Phillip W. Barth which appeared in the April, 1983 issue of Scientific American, pp. 44-55. Using this flow restriction technique, the aforementioned 2.5 factor increase of infusion rate when the patient travels from sea level to 10,000 feet altitude is reduced to a factor of 1.6. This accomplishes a significant improvement of infusion rate regulation without any weight increase, but the integral filter and multiple orifice restrictor may be somewhat more expensive than the capillary groove type because the filter and orifice features are smaller and processing controls need to be more exact to hold closer dimensional tolerances.

BRIEF DESCRIPTION OF THE DRAWINGS

The invention, both as to its organization and method of operation, together with further objects and advantages thereof, will best be understood by reference to the following specification taken in connection with the accompanying drawings, in which.

Referring now to the drawings, and more particularly to FIGS. 1-9 thereof, the implantable medication infusion device of the present invention is therein illustrated as comprising a flat circular housing, indicated generally at 10, which is formed oy the opposed dish-shaped circular members 12 and 14. A flexible corrugated diaphragm 16 is positioned between the members 12 and 14 to define a medication reservoir 18 and a pressure stabilizing chamber 20 with the members 12 and 14, respectively. A manifold body indicated generally at 22 is offset from the edge of the housing 10 and is connected to the housing member 12 through a neck portion indicated generally at 24, the body 22 being positioned in line with the housing 10 so that the overall thickness of the implantable device of the present invention is minimized. More particularly, the neck portion 24 includes a fan shaped portion 26 (FIG. 1) which is secured to the member 12 at the edge 28 thereof by welding or brazing, and a central raised portion 30 within which the passageway 32 is provided. The passageway 32 interconnects a recess 34 in the manifold body 22 and the reservoir 18 through a body stem element 36 having the central opening 38 therein.

An integral medication filter and capillary unit indicated generally at 40 is resiliently mounted within the recess 34, the unit 40 being preferaoly constructed and arranged as described in detail hereinafter in connection with FIGS. 5 and 6. Specifically, a first O-ring 42 is positioned in the groove 44 formed in the bottom of the recess 34 and an O-ring 46 is positioned immediately above the O-ring 42 in a groove 48 formed in the recess cover member 50 which is sealed to the housing 22 by means of the weld 52 after the unit 40 has been installed.

In order to permit refilling of the reservoir 18, a penetrable septum 60 is mounted in the body 22 so that a hypodermic needle may be inserted through the septum 60 into the chamber 62 formed in a needle stop member 64, the needle being inserted until it strikes the wall 66 of the needle stop 64. The needle stop 64 is sealed to the body 22 by means of the weld 68 after the penetrable septum 60 has been positioned in the stepped recess 70 formed in the body 22. The septum 60 may be made of medical grade silicone elastomer or medical grade bromobutyl elastomer. Bromobutyl elastomer is preferred because of its lower permeation rate, both for permeation of the medication out of the septum 60 and also for permeation into the septum of the dissolved gases in the body fluids which surround the implanted device.

The needle stop 64 is provided with a passage 72 which communicates with the recess 34 in the body 22 through the passageway 74 therein. The body 22 is provided with a slightly raised conical section 76 which is provided with the flared central recess 78 communicating with the septum 60, the flared walls 80 of the recess 78 acting to guide the needle to the surface 82 of the septum 60 as the needle is inserted. The slightly raised portion 76 with its central recess 78 facilitates the location of the implanted device by the doctor during a refilling operation. Once a needle has been inserted into the chamber 62, medication can be supplied from this chamber through the passageway 72, 74, the recess 34, the passageway 32 in the neck portion 30 and the central opening of the body stem 36 into the medication reservoir 18. A standard disposable syringe and hypodermic needle can be used to refill the implanted device. It will be noted that during this filling procedure the integral filter and capillary unit 40 is effectively bypassed since the chamber 34 communicates directly with the passageway 32 leading to the reservoir 18.

The pressure stabilizing chamber 20 is filled with a fluid which through a change of state establishes a substantially constant pressure on the medication within the reservoir 18 despite changes in the volume of medication within this reservoir and changes in temperature and pressure within the body. The pressure stabilizing chamber 20 may be filled in accordance with the procedure described in detail in my copending application Ser. No. 554,197, filed Nov. 22, 1983, and reference may be had to said application for a detailed description of such filling procedure. However, since the implantable device of the present invention is arranged to provide a continuous unprogrammed flow of medication into the body in response to this constant pressure, the two phase fluid must establish a stabilized pressure which is substantially above body pressure in order to force the medication through the filter and capillary unit 40 and into the body. Accordingly, the chamber 20 is preferably filled with a perfluorocarbon compound which is preferably of the type No. FC-87 or FC-88 manufactured by Minnesota Mining and Manufacturing Company, Inc. At body temperature this fluid creates a pressure of about 17.5 psia so that at an atmospheric pressure of 14.7 psia approximately 2.8 psi is available to drive the medication through the unit 40 and into the body.

Figure 8:
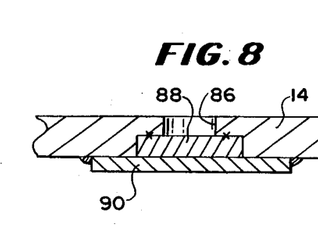
FIG. 8 is a fragmentary sectional view similar to FIG. 2 but on an expanded scale and showing the pressure stabilizing chamber seal of the implantable device.

During the filling procedure the outer edge of the diaphragm 16 is sealed to the outer lip portion 84 of the housing member 14 before the members 12 and 14 are joined together. This subassembly is then clamped to a fixture which simulates the curved surface of the member 12 so that a simulated reservoir 18 is provided between the diaphragm 16 and this fixture. A small central opening 86 FIG. 8 is provided in the member 14 through which the perfluorocarbon fluid is admitted.

Considering now the manner in which the chamber 20 is filled and sealed, the perfluorocarbon fluid is first vacuum conditioned to remove most of the absorbed air. This fluid and the simulated reservoir-pressure chamber subassembly are then heated to 90° F. After a vacuum is pulled in the chamber 20 and in the simulated reservoir 18 in the fixture, the heated perfluorocarbon fluid is introduced into both of these chambers so that initially there is no pressure differential across the diaphragm 16. A 10 to 20 psig nitrogen (or air) gas pressure is then applied through the fixture to the medication side of the diaphragm 16 which expels most of the perfluorocarbon fluid within the chamber 20 out of the hole 86 and firmly positions the diaghragm 16 against the housing member 14. However, a small amount of fluid remains in the chamber 20 between the corrugations of the diaphragm 16. The plug 88 is resistance welded into the hole 86 while being submerged in the expelled perfluorocarbon fluid to prevent the introduction of air into the chamber 20. The 10 to 20 psig nitrogen gas pressure is then removed and the pressure chamber subassembly cools to room temperature thus causing a "mechanical" volume of the chamber 20 to increase slightly due to the spring back in the diaphragm 16 and also causing the fluid volume of the perfluorocarbon fluid to reduce slightly due to the bulk temperature coefficient. The total of these two volume changes causes a small fluid vapor bubble to be formed in the chamber 20 that is equal in size to this total volume change. This vapor bubble acts as a nucleation site to initiate immediate and proper vaporization of the perfluorocarbon fluid as medication is removed from the chamber 18 and the diaphragm 16 moves away from the housing member 14.

After the chamber 20 is filled the plug 88 is resistance welded into the housing member 14 to seal the perfluorocarbon fluid into the chamber 20. Since this seal cannot be leak tested, a redundant seal is provided by TIG, laser or electron beam welding a thin piece of titanium 90 over the plug 88, as shown in FIG. 8, before the subassembly comprising the housing member 14 and the diaphragm 16 is assembled to the member 12. After the sealing plate 90 has been welded in place, this subassembly is sealed to the outer edge portion 92 of the upper housing member 12 by TIG, laser or electron beam meltdown welding to provide the completed housing 10. However, before this operation, a leak testable seal is established between the neck portion 24 and the upper housing member 12. More particularly, before the members 12, 14 are welded together, the body stem 36 is first welded to the neck portion 24 as indicated by the weld 94 (FIG. 7) before the neck portion 24 is brazed or resistance welded to the member 12. After the body stem 36 has been welded to the neck portion 24 the neck portion is brazed or resistance welded to the member 12 and the body stem 36 is also welded to the member 12 by means of the weld 96. After these operations have been performed the housing member 14 is then welded to the outer lip portion 92 of the member 12.

As discussed heretofore, it is also possible to use Freon 11, also called Freon MF, which is produced by the E. I. DuPont Company and has a vapor pressure equal to 23 psia at 98.6° F., in place of the FC-87 or FC-88 perfluorocarbon fluid (vapor pressure of 17.5 psia at 98.6° F.). The same filling procedure described in detail above for the perfluorocarbon fluid is employed to fill the pressure stabilizing chamber 20 with Freon 11. When the chamber 20 is filled with Freon 11 the undesired variation of infusion rate due to altitude and temperature changes is greatly reduced, as described heretofore.

Figure 1:
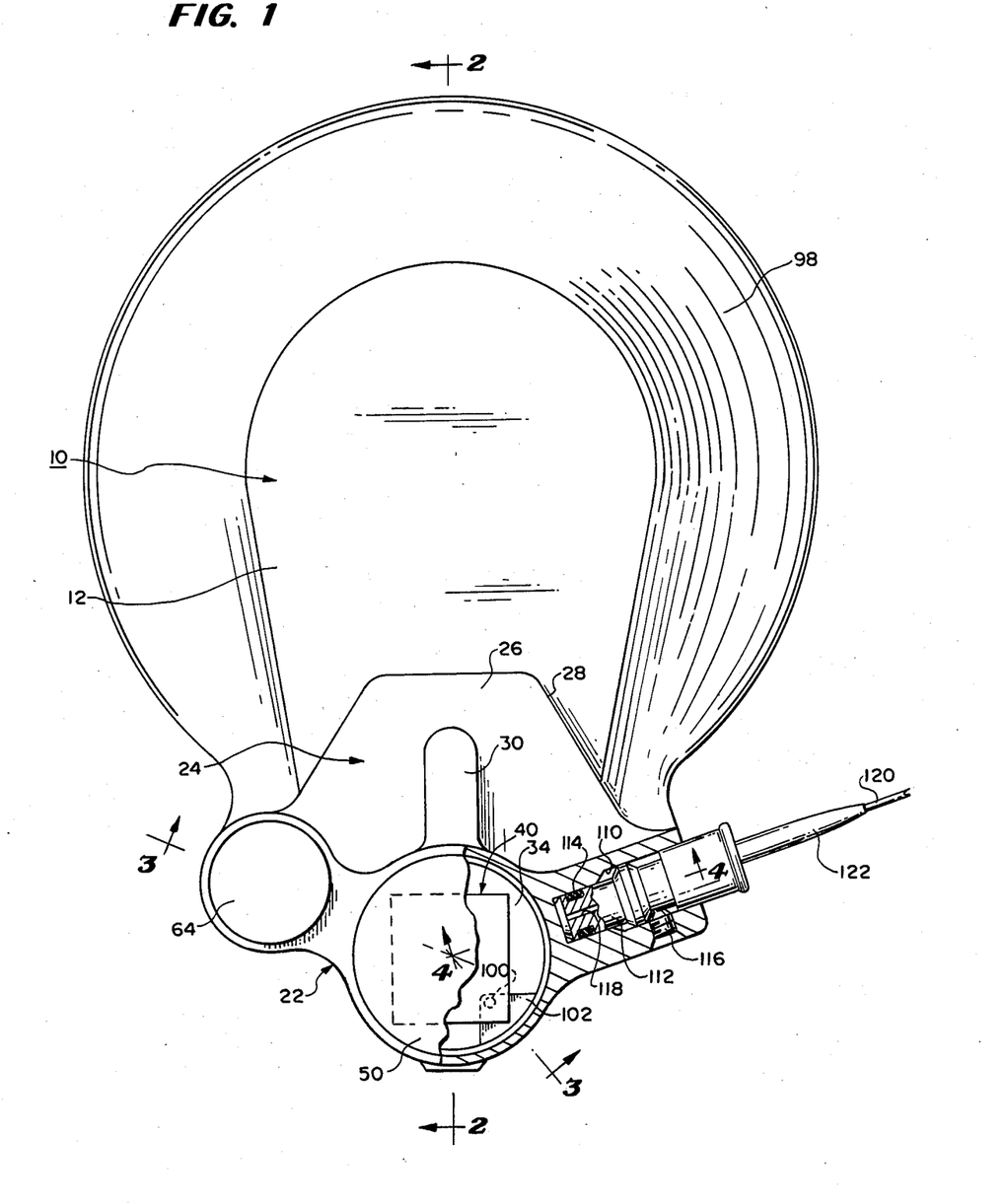
FIG. 1 is a plan view of the implantable medication infusion device of the present invention.
Figure 2:
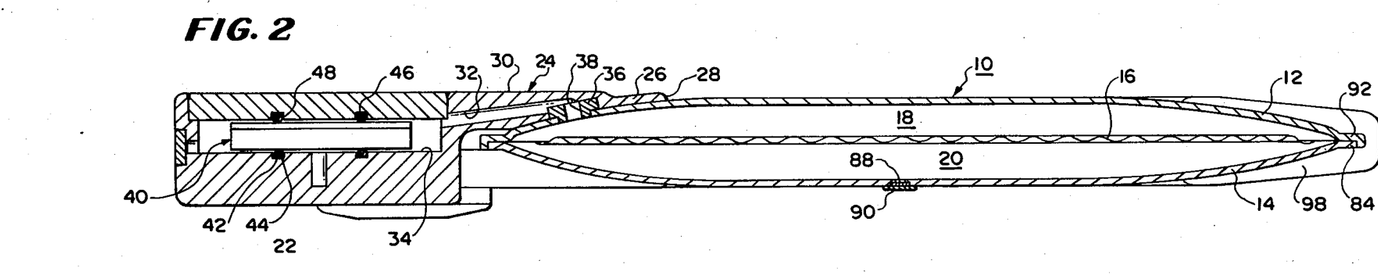
FIG. 2 is a sectional view taken along the lines 2—2 of FIG. 1.
Figure 3:
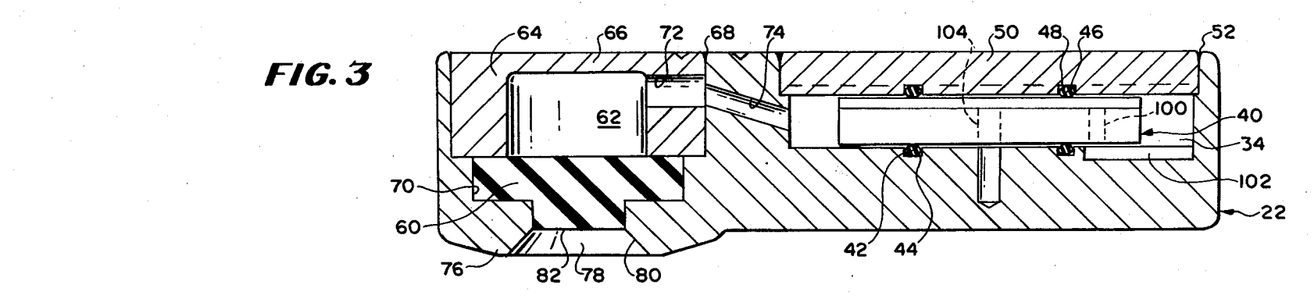
FIG. 3 is a sectional view taken along the lines 3—3 of FIG. 1.
Figures 4, 7:
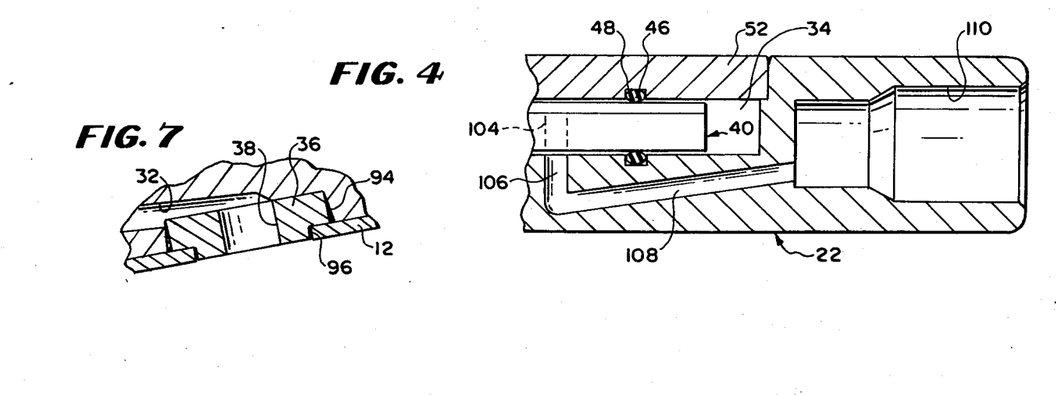
FIG. 4 is a sectional view taken along the lines 4—4 of FIG. 1 but with the catheter assembly omitted.
FIG. 7 is a fragmentary sectional view similar to FIG. 2 but on an expanded scale and showing the body stem-reservoir seal of the implantable device.

In order to protect the patient against any possible injury due to sharp edges of the housing 10, a silicone cover 98 is placed over the outer edge of the housing 10, the cover 98 extending around the entire periphery of the housing 10 to a point adjacent the body 22, as is clearly illustrated in FIG. 1.

Considering now the manner in which medication in the reservoir 18 is forced through the unit 40 and out of the manifold body 22, the integral filter and capillary unit 40 is provided with the transverse inlet opening 100 in one corner thereof which is positioned above a quadrant shaped recess 102 in the bottom wall of the chamber 34. The unit 40 is also provided with a transverse, central outlet opening 104 which is positioned above the transverse end portion 106 of a passageway 108 provided in the body 22. The O-ring 42 provides a seal between the inlet 100 and the outlet 104 of the unit 40. Alternatively, an additional O-ring concentric with O-ring 42 can be used to provide a redundant O-ring seal. If desired, the recess 102 may be in the form of an annular recess in the bottom wall of the chamber, this annular recess permitting access to the inlet 100 irrespective of the orientation of the unit 40 within the chamber 34.

The passageway 108 communicates with a side opening recess 110 which is provided in the body 22 and is adapted to receive a catheter assembly, as shown in FIG. 1. More particularly, this catheter assembly comprises a main body member 112 which is sealed within the recess 110 by means of the O-ring 114 and is held in place by the set screw 116. The body 112 is preferably made of medical grade silicone elastomer, or other biocompatible material, and is provided with the central passageway 118 which extends to the flexible catheter tube 120 the end of which is secured in an end recess in the body 112 by any suitable means such as by a silicone adhesive or by a vulcanizing process. A tapered sleeve 122 is provided to prevent excessive bending of the catheter tube 120 when it is placed at the desired infusion site within the body. It will be noted that during the supply of medication through the unit 40 to the catheter outlet the medication flows in the reverse direction through the passageway 32 from that of the filling operation. Preferably, all of the component parts of the implantable medication infusion device of the present invention, except for the septum 60, flow restrictor unit 40 and catheter 112, are made of titanium which is more compatible, both to the medication and to the body, than a stainless steel or a titanium alloy.

Figure 5:
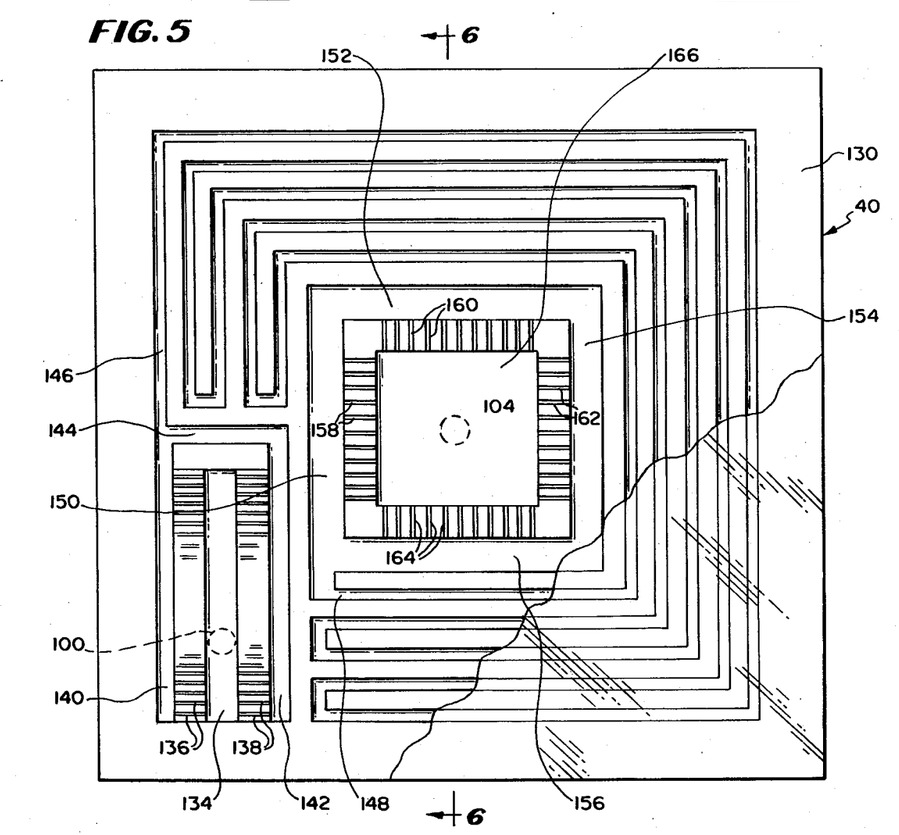
FIG. 5 is a greatly expanded plan view of the integral fluid filter and capillary unit employed in the device of FIG. 1.
Figure 6:
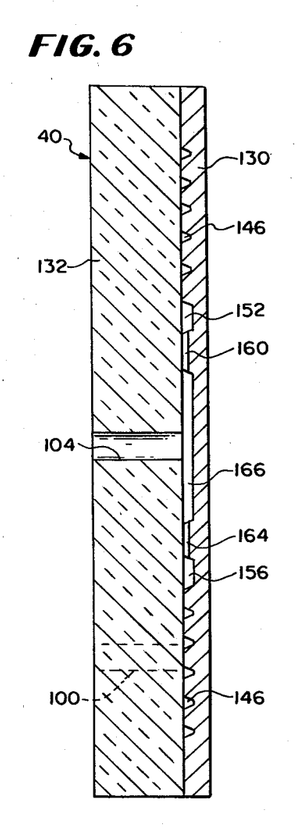
FIG. 6 is a sectional view taken along the lines 6—6 of FIG. 5.
Figure 9:
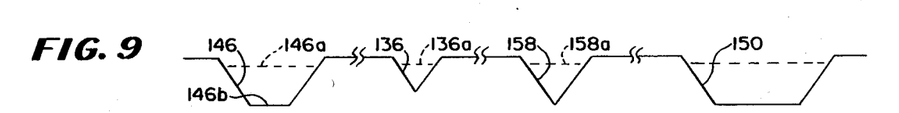
FIG. 9 is a sectional view similar to FIG. 6 but on an enlarged scale of the different groove configurations in the integral filter and capillary unit of the implantable device of FIG. 1.

Considering now the integral filter and capillary unit 40, and referring to FIGS. 5 and 6 wherein this unit is shown on a greatly expanded scale, the unit 40 comprises a square silicon substrate 130 approximately ⅜ of an inch on each side and having a thickness of about 0.010 inches. The substrate 130 is electrostatically bonded to a glass plate 132 of a size similar to the substrate 130 and having a thickness of about 0.040 inches. The plate 132 is provided with the transverse inlet opening 100 and outlet opening 104 which communicate with different grooved areas on the substrate 130. More particularly, the inlet opening 100 communicates with a collector channel 134 which is positioned between two groups of transversely extending, parallel inlet filter grooves 136 and 138 formed in the surface of the substrate 130. Medication which is forced through the filter grooves 136, 138 is collected in the collector channels 140, 142 and 144 formed in the surface of the substrate 130, which supply filtered medication to the inlet of a capillary groove 146 which is formed in the surface of the substrate 130 and extends in a series of reentrant loops to an outlet portion 148 thereof. The outlet 148 of the capillary groove 146 communicates with collector channels 150, 152, 154 and 156 also formed in the surface of the substrate 130. The collector channels 150–156 communicate with four groups of parallel outlet filter grooves 158, 160, 162 and 164 which are arranged around the four sides of the rectangular outlet collector area 166 formed in the surface of the substrate 130 at the center thereof. Medication which then passes through the outlet filter grooves 158–164 is collected in the area 166 and supplied through the transverse outlet 104 in the glass plate 132, and through the channel 108 in the body 22 to the catheter outlet described heretofore. All of the above described grooves, channels and collector areas are preferably formed in the surface of the silicon substrate 130 by a single operation using semiconductor processing and micromachining techniques, as described in detail in the aoove identified Barth application Ser. No. 616,658 and in an article entitled "Silicon Micromechanical Devices" by James B. Angell, Stephen C. Terry and Phillip W. Barth which appeared in the April, 1983 issue of Scientific American, pp. 44–55. The substrate 130 is preferably a single silicon crystal in which the [100] plane is oriented parallel to the surface of the substrate 130 in which the grooves and collector channels are formed. Also, an anisotropic etchant is preferably employed which etches at different rates in different directions in the crystal lattice so that sharp edges and corners are formed during the etching process. Suitable anisotropic etchants are hot alkaline solutions such as aqueous potassium hydroxide (KOH), aqueous sodium hydroxide (NaOH) and a mixture of ethylenediamine, pyrocatechol, and water, known as EDP. As described in detail in the above identified Angell et al article, with such ansiotropic etchants flat bottomed grooves can be formed in a [100] crystal by stopping the etching operation before the point of intersection of the [111] planes is reached. Accordingly, by starting with exposed areas of different widths for the inlet filter grooves 136, 138, the outlet filter grooves 158–164, the capillary groove 146 and the collector channels, all of the grooves and collector channels may be formed in a single etching operation. More particularly, as shown in FIG. 9, as the etching operation proceeds the sidewalls of the grooves slope inwardly along the [111] planes of the substrate 130 but the bottom of the groove remains parallel to the surface of this substrate. Thus, considering the capillary groove 146, at the start of the etching operation the bottom of the groove is shown by the dotted line 146a, the final groove being shown in solid lines in this figure as having the narrower flat bottom portion 146b. With regard to the inlet filter grooves 136, which are initially much narrower than the capillary groove area, in the early portion of the etching process the flat bottom portion 136a is produced, as shown in dotted lines in FIG. 9. However, before the end of the etching operation the point of intersection of the [111] planes is reached to provide a sharp V groove which is shallower than the capillary groove 146. In a similar manner, the outlet filter grooves 158 which are somewhat wider than the inlet filter grooves 136 have the initial flat bottom portion 158a at the beginning of the etching operation. However, by the end of the etching operation the deeper sharp V groove 158 is formed which is of the same depth as the capillary groove 146 and is of substantially greater cross sectional area than the inlet filter grooves 136. The collector channels 150 are also formed during the same etching operation and have a much wider flat bottom portion since they are of substantially greater width than the capillary groove 146.

Preferably, the cross sectional area of the inlet filter grooves 136, 138 is substantially smaller than the cross sectional area of the outlet filter grooves 158–164. With such an arrangement the outlet filter grooves 158–164 can trap particles which might plug the capillary under backflow conditions wnich could occur during construction and testing of the implantable device of FIG. 1. However, the outlet filter grooves 158–164 should not clog with particles which are small enough to pass through the inlet filter grooves 136, 138 and the capillary groove 146 in the normal flow direction. Preferably the inlet filter grooves 136, 138 are 28 microns wide, the outlet filter grooves 158–164 are 39 microns wide, and the capillary groove 146 is 50 microns wide, 20 microns deep and 6.4 inches long for a nominal (98.6° F., sea level) infusion rate of 10 microliters per hour of 100 unit insulin. All of the wall portions of the grooves 136, 138, 158–164 and 146 slope inwardly and downwardly at an angle of 54.74 degrees relative to the horizontal, i.e. along the [111] plane of the crystal substrate 130. The number of inlet filter grooves 136, 138 is preferably such that the total flow area of these grooves is about 120 times the flow area of the capillary groove 146. The number of outlet grooves 158–164 is such that the total flow area of these grooves is about 200 times the flow area of the capillary groove 146.

The substrate 130 and glass plate 132 are preferably bonded by providing optically flat surfaces on the opposed surfaces of these parts. They are then heated to a temperature of about 400° C. and a potential of about 1200 volts DC is applied across the assemoled parts 130 and 132 for about 15 minutes to create an electrostatic bonding force. During this bonding operation the negative terminal of the 1200 volt D.C. supply is connected to the glass plate 132. The parts may either be heated first and then the voltage applied or the voltage may be applied and the parts then heated. No external pressure is applied in such an electrostatic bonding operation and very little stress is produced as a result thereof because both the substrate 130 and the glass plate 132 have substantially the same temperature coefficient of expansion. Preferably, the glass plate 132 is a tybe 7740 Pyrex borosilicate glass manufactured by Corning Glass Works.

Preferably, a large number of the silicon substrates 130 are formed from a single large silicon wafer so that inlet and outlet filter grooves and the capillary groove 146 are of highly uniform dimensions and the substrates 130 formed from the common wafer will have substantially identical flow rates through the capillary groove 146 thereof. After this large wafer is completed in accordance with the processing technique described above, a glass plate of similar size is electrostatically bonded to the wafer, as described heretofore, and the resultant multilayer unit is then diced into squares by a diamond saw to provide the units 40. With such an arrangement different flow rates may be accurately provided for a large number of units 40 by simply varying the initial width of the unmasked area of the substrate surface corresponding to the capillary groove 146 or by changing the etching time and depth of the capillary groove. It is thus ppssible to provide implantable devices having accurately predetermined flow rates by simply choosing a unit 40 having a desired flow rate of 10 microliters per hour, 15 microliters per hour, etc. and mounting it in the body 22 in the manner described in detail heretofore.

During the dicing operation tape is placed over the holes 100 and 104 in the glass plate 132 to prevent contamination of the filter grooves by the duct from the diamond saw. The holes 100 and 104 in the glass plate 132 may either be made mechanically by an abrasive vapor blasting technique or they can be laser drilled. In either case, tne holes 100 and 104 will be tapered inwardly somewhat when formed using these techniques, as will be readily understood by those skilled in the art.

If desired, the integral filter and capillary unit 40 may be mounted in the chamber 34 with the silicon substrate 130 on the bottom adjacent the passage 106 in the manifold 22. In such case, openings corresponding to the holes 100 and 104 are provided in the silicon substrate 130 rather than in the glass plate 132.

Figures 10, 12:
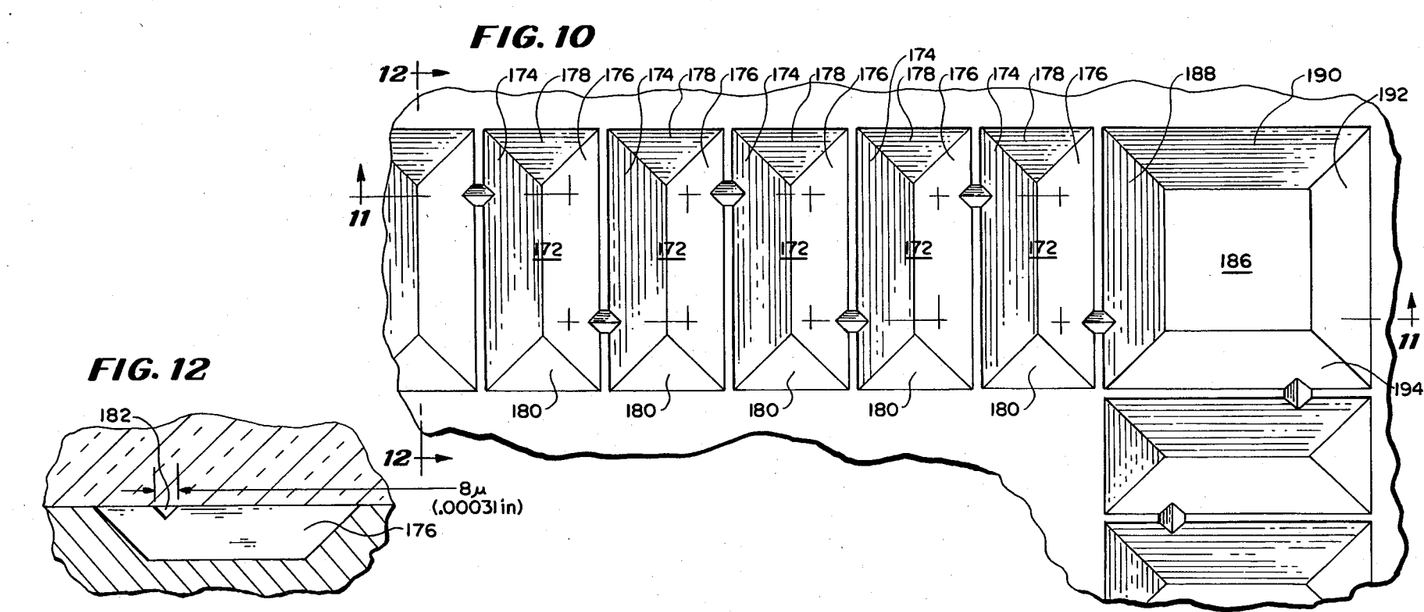
FIG. 10 is a fragmentary plan view of an alternative embodiment employing a multiple orifice flow restrictor.
FIG. 12 is a sectional view taken along line 12—12 of FIG. 10.
Figure 11:
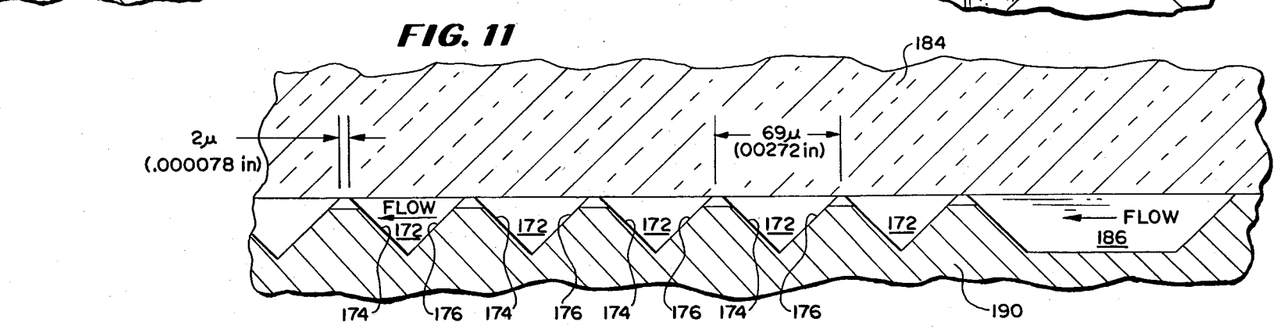
FIG. 11 is a sectional view taken along line 11—11 of FIG. 10.

In accordance with an alternaive embodiment of the invention, the capillary groove 146 may be replaced by a multiple orifice restrictor arrangement, as shown in FIGS. 10, 11 and 12 in order to reduce the above described variation in infusion rate due to altitude and temperature changes. Referring to these figures, a series of miniature orifices are formed in the silicon substrate 170 which is preferably a single silicon crystal in which the [100] plane is oriented parallel to the surface of the substrate 170. These miniature orifices are formed in the substrate 170 by first anisotropically etching the tranverse V shaped channels 172 which are positioned along the flow path of the multiple orifice restrictor unit. The channels 172 have sloping side walls 174 and 176 and sloping end walls 178 and 180 all of which extend downwardly at an angle of 54.74° to the horizontal along the [111] plane of the crystal 170. The channels 172 preferably have a transverse length at the surface of the substrate 170 of 90 microns and a width along the flow path of 69 microns. Each channel 172 is separated from the next one by 2 microns.

Before the channels 172 are formed in the substrates 170, a series of staggered orifices are initially formed in the surface of substrate 170 in the areas separating the transversely extending channels 172 by anisotropically etching the small longitudinally extending V-shaped grooves 182. The grooves 182 have a width of 8 microns and are etched to a depth of 5.7 microns (0.00022 inches), the walls thereof sloping inwardly at an angle of 54.74° to the horizontal. Preferably, the initial surface areas provided to form the grooves 182 will have a width of 8 microns and a length along the flow path of approximately 15 microns, the sloping end walls of the grooves 182 being etched away when the grooves 172 are formed, so that the final shape of the grooves 182 is as illustrated in FIGS. 10, 11 and 12. When the glass plate 184 is placed on the upper surface of the substrate 170 and bonded thereto, in the manner described heretofore in connection with the integral filter and capillary unit 40, a series of microminiature precision orifices are formed by the V-shaped longitudinally extending grooves 182 which are of extremely small dimensions and are much smaller and dimensionally more accurate than would be possible by conventional metal machining or chemical milling in a metal such as titanium. As clearly shown in FIG. 10, the grooves 182 are preferably staggered along the length of the walls separating the channel 172 to provide additional flow restriction.

In the embodiment of FIGS. 10, 11 and 12 the transverse channels 172 extend along a flow path generally similar to the reentrant path of the capillary groove 146 in the substrate 130 of FIGS. 5 and 6. At the right angle turns of the flow path of FIGS. 10, 11 and 12 a square, flat bottomed channel 186 is formed in the substrate 170 by anisotropic etching at the same time the V-shaped channels 172 are formed, the channel 186 having the four sloping wall portions 188, 190, 192 and 194 which extend along the [111] plane of the crystal at an angle of 54.74 degrees relative to the horizontal. The small V-shaped orifice grooves 182 are then formed in the wall portions 188 and 194 of the channel 186 at the same time the rest of the grooves 182 are formed in the substrate 170.

In the embodiment of FIGS. 10, 11 and 12 the substrate 170 and glass plate have the same overall dimensions as the unit 40 described in detail heretofore. Also, the inlet filter grooves 136, 138, outlet filter grooves 156-164 and collector channels 134, 140, 142, 144 and 150-156 are all formed in the substrate 170 at the same time the V-shaped channels 172 are formed therein. However, both the inlet filter grooves 136, 138 and the outlet filter grooves 156-164 are considerably narrower in the embodiment of FIGS. 10, 11 and 12 to provide proper filtering for the orifices formed by the V-grooves 182. Preferably, the inlet filter grooves 136, 138 have a width of 4 microns and the outlet filter grooves 156-146 have a width of 6 microns in the multiple orifice embodiment of FIGS. 10, 11 and 12.

As discussed generally heretofore, the flow rate through an orifice, such as the orifices formed by the V-grooves 182 in the substrate 170, is proportional to the square root of the pressure drop across the orifice whereas the flow rate in the capillary groove 146 of FIGS. 5 and 6 is directly proportional to the pressure drop thereacross. Accordingly, for a given change in the pressure drop across the restrictor, due to altitude and temperature variations, the variation in flow rate of the mutliple orifice restrictor of FIGS. 10, 11 and 12 will be substantially less than the capillary groove arrangement of FIGS. 5 and 6. For example, a change in pressure when traveling from sea level to 10,000 feet altitude may cause the flow rate of the capillary groove arrangement of FIGS. 5 and 6 to vary by a factor of 2.5 (with an FC-87 pressurant) whereas this change in pressure would theoretically cause the flow rate of the multiple orifice arrangement of FIGS. 10, 11 and 12 to vary oy only a factor of 1.6. This factor is closer to 1.7 in actual practice due to the imperfect orifice conditions around the grooves 182. Nevertheless, it will be seen that a substantial reduction in the undesired variation of flow rate with changes in altitude and temperature is achieved with the embodiment of FIGS. 10, 11 and 12.

Since the infusion rate of an implantable device is very slow, there is a very low velocity pressure developed by each of the orifices in the embodiment of FIGS. 10, 11 and 12 and a large number of orifices is required to create a sufficient pressure drop. For example, when the grooves 182 have the dimensions and spacing described heretofore, approximately 2530 orifices are required to limit the infusion rate to 10 microliters per hour using FC-87 or FC-88 perfluorocarbon pressurant at normal body temperature, i.e. 98.6° F.

While there have been illustrated and described several embodiments of the present invention, it will be apparent that various changes and modifications thereof will occur to those skilled in the art. It is intended in the appended claims to cover all such changes and modifications as fall within the true spirit and scope of tne present invention.

What is claimed as new and desired to be secured by Letters Patent of the United States is:

1. An implantable medication infusion device, comprising a pair of circular concave members positioned in opposed relation with the outer edges thereof connected together, a flexible circular diaphragm positioned between said concave members and having the edge thereof sealed to said concave members thereby to form a pressure stabilizing chamber with one of said concave members on one side of said diaphragm and a medication reservoir with the other one of said concave members on the other side of said diaphragm, a two phase fluid in said pressure stabilizing chamber for maintaining a constant pressure on said diaphragm which is greater than the body pressure of the body in which said infusion device is implanted, body means secured to at least one of said concave members and having a recess therein, a penetrable septum mounted in said body means and communicating with said recess a passageway in said body means between said recess and said reservoir, whereby said reservoir can be filled through said septum, said recess and said passageway, and a capillary unit positioned in said body means and having an inlet connected to said reservoir and an outlet communicating with the exterior of said device, said capillary unit having a flow restrictive passageway between said inlet and outlet of sufficiently small cross section to limit the flow of medication from said reservoir in response to the pressure on said diaphragm to a desired rate.

2. The medication infusion device of claim 1, wherein said capillary unit comprises a silicon substrate having a capillary groove formed in one surface thereof and connected between said inlet and said outlet, and a glass plate bonded to said surface of said silicon substrate to form with said substrate said flow restrictive passageway.

3. The device of claim 2, which includes means for establishing a seal between said inlet and said outlet of said capillary unit positioned in said body means.

4. The device of claim 3, wherein said capillary unit is positioned in an opening in one side of said body means and a cover is seated in said opening, said sealing means comprising first O-ring means between said capillary unit and said cover and second O-ring means between said capillary unit and said opening in said body means.

5. The device of claim 4, wherein said body means includes a second passageway extending from the bottom of said recess inside said second O-ring means to the exterior of said body.

6. The device of claim 2, wherein said inlet of said capillary unit comprises a first opening in said plate and communicating with one end of said groove, and said outlet comprises a second opening in said glass plate and communicating with the other end of said groove.

7. The device of claim 2, wherein said capillary unit also includes inlet filter means connected between said inlet and one end of said capillary groove, and outlet filter means connected between the other end of said capillary groove and said outlet.

8. The device of claim 7, wherein said inlet filter means comprises a first series of parallel grooves in said silicon substrate and said outlet filter means comprises a second series of parallel grooves in said silicon substrate, the cross sectional area of the grooves in said second series being substantially greater than the cross sectional area of the grooves in said first series.

9. The device of claim 8, wherein said inlet includes an opening in said glass plate and said first series of parallel grooves are positioned in groups around said opening.

10. The device of claim 8, wherein said outlet includes an opening in said glass plate and said second series of parallel grooves are positioned in groups around said opening.

11. The device of claim 10, wherein said group of second parallel grooves are arranged along the four sides of a rectangle within which is positioned said opening.

12. The device of claim 11, which includes a collector groove formed in said surface and interconnecting the outer ends of all of said groups of second parallel grooves, said collector groove also being connected in said other end of said capillary groove.

13. The device of claim 8, wherein said inlet includes an opening in said silicon substrate and said first series of parallel grooves are positioned in groups around said opening.

14. The device of claim 8, wherein said outlet includes an opening in said silicon substrate and said second series of parallel grooves are positioned in groups around said opening.

15. The device of claim 2, wherein said inlet of said capillary unit comprises a first opening in said silicon substrate and communicating with one end of said groove, and said outlet comprises a second opening in said silicon substrate and communicating with the other end of said groove.

16. The device of claim 1, wherein said device has a maximum thickness of one half inch.

17. An implantable medication infusion device, comprising a pair of circular concave members positioned in opposed relation with the edges thereof connected together to form a housing, a flexible diaphragm mounted within said housing to provide a pressure stabilizing chamber with one of said concave members and a medication reservoir with the other of said concave members, a two-phase fluid in said pressure stabilizing chamber for maintaining a constant pressure on said diaphragm which is greater than the body pressure of the body in which said infusion device is implanted, a manifold body offset from the edge of said housing and having a neck portion connected to one of said concave members, said manifold body having a chamber therein which is connected to said reservoir through a passageway in said neck portion, a penetrable septum mounted in said body and communicating with said chamber, whereby said reservoir can be filled by supplying medication through said septum said chamber and said passageway, and a capillary unit positioned in said chamber and having an inlet connected to said chamber and an outlet communicating with the exterior of said device, said capillary unit having a flow restrictive conduit between said inlet and said outlet of sufficient length and having a sufficiently small cross section to limit to a desired rate the flow of medication from said reservoir and through said passageway in response to the pressure exerted on said diaphragm by said two-phase fluid.

18. The device of claim 17, wherein the thickness of said offset manifold body is approximately equal to the thickness of said housing.

19. An implantable medication infusion device, comprising a medication reservoir having a movable wall portion, a pressure stabilizing chamber in communication with said movable wall portion, a two phase fluid in said pressure stabilizing chamber for maintaining a constant pressure on said movable wall portion which is greater than the body pressure of the body in which said infusion device is implanted, a catheter outlet communicating with the exterior of said device, and a flow restrictor unit interposed between said reservoir and said catheter outlet, said flow restrictor unit comprising a large number of serially connected orifices which collectively limit the flow of medication from said reservoir in response to the pressure on said movable wall portion to a desired rate.

20. The medication infusion device of claim 19, wherein said flow restrictor unit comprises a silicon substrate having a large number of minute grooves formed in one surface thereof and serially interconnected along a predetermined flow path, and a glass plate bonded to said surface of said silicon substrate to form with said minute grooves a series of orifice type restrictions which collectively limit the flow of medication from said reservoir to said desired rate.

21. The medication infusion device of claim 20, wherein said minute grooves are interconnected by means of troughs formed in said surface of said silicon substrate which are of much greater depth than said minute grooves.

22. The medication infusion device of claim 21, wherein said troughs comprise V-shaped grooves formed in the surface of said substrate and extending transversely of said flow path.

23. The medication infusion device of claim 22, wherein said troughs have a length transverse to said flow path of approximately ninety microns.

24. The medication infusion device of claim 22, wherein said troughs have a width along said flow path of approximately sixty-nine microns.

25. The medication infusion device of claim 22, wherein said troughs have a depth of approximately twenty-eight microns.

26. The medication device of claim 22, wherein said troughs are spaced apart by approximately two microns along the surface of said substrate.

27. The medication infusion device of claim 20, wherein said minute grooves each have a width of approximately 8 microns.

28. The medication infusion device of claim 20, wherein said minute grooves each have a depth of 5.7 microns.

29. The medication infusion device of claim 20, which includes inlet filter means formed in said surface of said substrate and connected to one of said minute grooves at one end of said flow path.

30. The medication infusion device of claim 29, which includes outlet filter means formed in said surface of said substrate and connected to one of said minute grooves at the other end of said flow path.

31. The medication infusion device of claim 30, wherein said outlet filter means comprises a second series of parallel grooves formed in said surface of said silicon substrate and each having a width of approximately six microns.

32. The medication infusion device of claim 29, wherein said inlet filter means comprises a first series of parallel grooves formed in said surface of said silicon substrate and each having a width of approximately four microns.

* * * * *